United States Patent [19]

Van Duzer

[11] Patent Number: 4,620,908

[45] Date of Patent: Nov. 4, 1986

[54] METHOD FOR DESTROYING MICROBIAL CONTAMINATION IN PROTEIN MATERIALS

[75] Inventor: John P. Van Duzer, Huntington Beach, Calif.

[73] Assignee: Biocell Laboratories, Inc., Carson, Calif.

[21] Appl. No.: 622,019

[22] Filed: Jun. 18, 1984

Related U.S. Application Data

[63] Continuation-in-part of Ser. No. 538,562, Oct. 3, 1983, abandoned.

[51] Int. Cl.[4] .......................... C07G 7/00; A61L 2/00; A61K 41/00; B01J 19/08
[52] U.S. Cl. ................................. 204/157.68; 422/22; 422/23; 422/24; 424/101; 514/2
[58] Field of Search ............... 260/112 R, 112 B, 122; 422/22, 23, 24; 204/160.1

[56] References Cited

U.S. PATENT DOCUMENTS

| | | | |
|---|---|---|---|
| Re. 23,195 | 2/1950 | Brasch | 422/22 |
| 3,743,480 | 7/1973 | Falk | 260/112 B |
| 3,779,706 | 12/1973 | Nablo | 422/22 |
| 4,136,094 | 1/1979 | Condie | 260/122 |
| 4,251,437 | 2/1981 | Rasmussen et al. | 260/112 B |
| 4,330,626 | 5/1982 | Blair et al. | 422/22 X |
| 4,370,264 | 1/1983 | Kotitschke et al. | 260/112 B |

*Primary Examiner*—Howard E. Schain
*Attorney, Agent, or Firm*—Robert J. Schaap

[57] ABSTRACT

A method for destroying microbial contamination, such as viral and bacterial contamination and mycoplasma contamination, in protein material, and particularly tissue and serum from animals and human beings. The method comprises the reducing of the temperature of the protein material, in a state other than a lyophilized state, to at least the freezing point and preferably to the eutectic point. The method comprises reducing the temperature of lyophilized protein to at least a temperature of −3 degrees C., or colder. Thereafter, gamma radiation is applied in an amount sufficient, at least 5,000 rads and preferably at least 600,000 rads, to destroy substantially all microbial contamination in the protein material without significantly reducing the protein efficacy.

19 Claims, 1 Drawing Figure

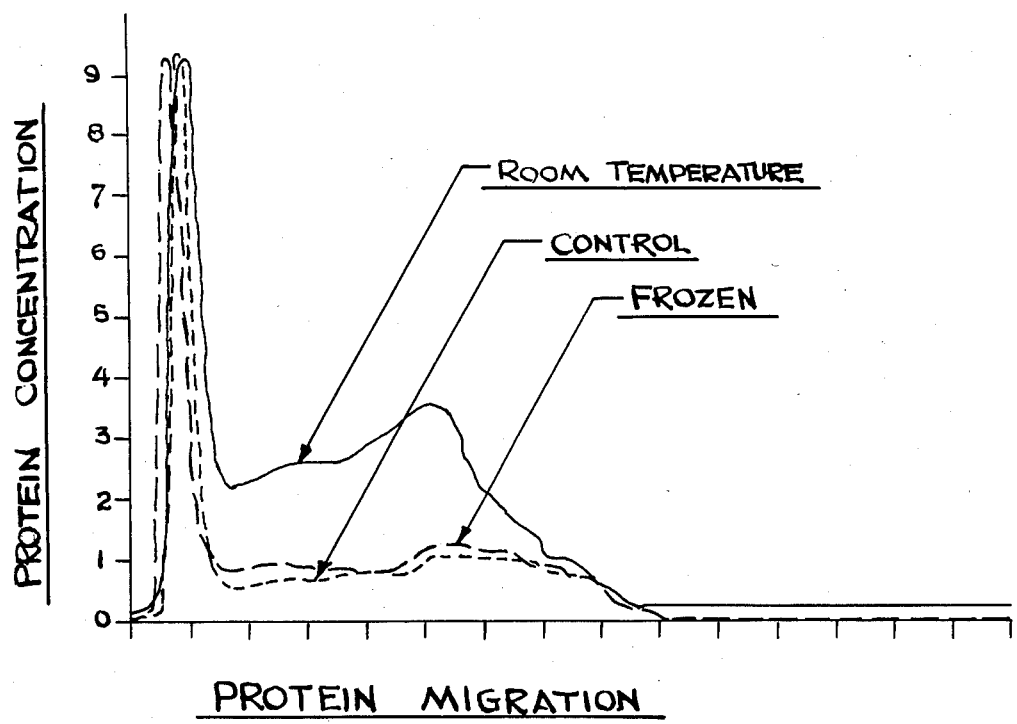

METHOD FOR DESTROYING MICROBIAL CONTAMINATION IN PROTEIN MATERIALS

RELATED APPLICATION

This application is a continuation-in-part of my copending application Ser. No. 538,562, dated Oct. 3, 1983 for "METHOD" FOR DESTROYING MICROBIAL CONTAMINATION IN PROTEIN MATERIALS", now abandoned.

BACKGROUND OF THE INVENTION

1. Field of the Invention

This invention relates in general to certain new and useful improvements in a method for destroying microbial contamination, and more particularly, to a method of destroying microbial contamination in protein material by reducing the temperature of the protein material and thereafter applying gamma radiation in an amount sufficient to destroy any microbial contamination.

2. Brief Description of the Prior Art

In recent years, it has been recognized that tissues and fluids from human beings and other animals can be used quite effectively in research activities and in various diagnostic and theraputic activities. However, particularly for in-vivo use, it is necessary to insure that the protein material, such as the tissue or serum from a human being or other animal, is relatively free from microbial contamination, such as viral and bacterial and mycoplasma contamination.

It is well known that various disease forms can be readily and easily transmitted through blood transfusions. For example, it has been recognized that hepatitus and more recently, the acquired immune deficiency syndrome (AIDS) is transmitted through blood serum, as for example, during blood transfusions, or injections of purified protein, such as factor VIII.

Testing for hepatitis can be conducted by testing for the $HB_5AG$ antigen. However, for most diseases and abnormal conditions, the only effective means for screening doners of blood serum is that of a verbal inquiry. In many cases, the donor may deceive the interviewer about his or her medical condition in order to collect a monetary fee for the donated blood. However, more frequently, the donor may not even recognize the presence of any potential microbial contamination in the blood serum due to the fact that there may be a relatively long incubation period. Heretofore, and presently, there has been no effective means for readily determining the presence of at least viral contamination in a body serum.

It is important to obtain tissue culture which are viral and bacteria and mycoplasma free. It is also of importance to provide a tissue culture sera for use in testing activities and in research activities and which sera is also free of microbial contamination. Tissue culture sera are widely used to investigate contamination of implants such as breast implants, contact lenses, etc. Tissue culture and the sera for the tissue culture, which is a source of nutrient for the tissue culture, are often used for the growth of other protein material and often used to similulate an in-vivo situation. For example, tissue cultures and tissue culture sera are widely used in the production of vaccines. Thus, it is quite important that both the tissue culture and the tissue culture sera be free of any microbial contamination.

At present, it takes at very minimum, six weeks and oftentimes three months or longer to certify a fluid as free from such contamination. In order to determine whether or not there is any contamination, a cell regeneration is made and the viral activity is measured. Typically, techniques of this type, wherein cytopathological effect (CPE) is measured for viruses, are well known.

There have been attempts to measure the antigen level in a donors blood in order to determine whether or not viral activity was present. However, in many cases, it is virtually impossible to detect the virus by virtue of antigen level. This may be due to the fact that the virus may not have developed to a state where antigen is present. Thus, the viral contamination is incipient and may grow after such testing to a point where contamination is serious and thereby affect the recipient of any such tissue or serum.

It is possible to detect viral contamination by electron microscope measurements. However, these microscopes are very costly, require experience and known-how to operate and are generally not available at blood donor stations. Further, even if the microscopes could be provided, analysis would be time consuming and not effective due to the low concentration of virus is many infections. Thus, microscopic examination is an impractical method in most cases, and particularly in blood donations.

Heat treatment has been used for certifying albumin and other proteinaceous substances. In the case of albumin, the albumin is heated to at least 60 degrees C. for about ten hours. This has been found to be moderately effective for certifying albumin, although in many cases, it may not destroy all known bacterial and viral forms. In addition, this technique is not effective for many protein forms inasmuch as it may tend to significantly reduce the efficacy of the protein form.

Irradiation of blood components has been proposed, as for example, in "The Effects of Irradiation on Blood Components" by L. N. Button et al, presented in the American Association of Blood Banks annual meeting and accepted for publication May 18, 1980. This article describes cesium radiation with dosages varying from 500 to 8,000 rads and the article is only concerned with the destruction of lymphocytes in blood. This dosage is generally not believed to be sufficient to effectively destroy all contamination and further there is no suggestion of reducing temperature to protect the protein material.

It has been recognized that the method of certifying animal or human tissue or serum by anaylzing tissue or serum for presence of microbial contamination, is not truly effective. Therefore, more recent efforts have turned to some means or method for destroying the microbial contamination in the fluid thereby obviating the need for analysis. Further, there is a clear recognized need for some means or method for insuring certification of protein matter and particularly body serum, such as blood serums, by effectively destroying microbial contamination without substantially reducing the efficacy of the protein material.

OBJECTS OF THE INVENTION

It is, therefore, one of the primary objects of the present invention to provide a method of reducing microbial contamination in protein material, while maintaining protein efficacy, by reducing the temperature of the protein material to a low temperature range and thereafter applying gamma radiation to the protein material while at the reduced temperature.

It is another object of the present invention to provide a method of the type stated in which the protein material is reduced to a temperature which is at least as low as the freezing point and preferably below the eutectic point of the material.

It is a further object of the present invention to provide a method of the type stated in which gamma radiation in an amount of at least 5,000 rads is applied to the protein material while in a reduced temperature state.

It is an additional object of the present invention to provide a method of the type stated which is highly effective in reducing microbial contamination and does not substantially adversely affect the overall efficacy of the protein material.

It is still another object of the present invention to provide a protein material which is relatively free from contamination by reducing the temperature of the protein material to a selected low temperature and thereafter applying gamma radiation in a selected amount.

It is another salient object of the present invention to provide a method of enabling the certification of protein material, such as body serums and body tissue and protein materials derived therefrom as well as protein material generated in an in-vitro environment, by effectively destroying the microbial contamination without adversely substantially affecting the overall efficacy of the protein material.

It is also an object of the present invention to provide whole body serums and components of the body system in a relatively contamination free state and which thereby minimizes risk in use of such material on an in-vivo basis.

It is still another object of the present invention to substantially reduce the infectious rate of contagious diseases by providing body tissue and serum which is virtually free of microbial contamination.

With the above and other objects in view, my invention resides in the novel features and forms of the method and in the products produced thereby as presently described and pointed out in the claims.

BRIEF SUMMARY OF THE DISCLOSURE

The present invention relates to a method of destroying microbial contamination in protein material and rendering such material relatively free from such microbial contamination without substantially adversely affecting the overall efficacy of the protein material. The method comprises the reducing of the temperature of the non-lyophilized protein material, e.g. when in a state other than a lyophilized state, to the freezing point and preferably to the eutectic point. When the protein material is in a lypholized form it is desirable to reduce the temperature to at least $-3$ degrees C., although the temperature of solid or semi-solid protein material may be reduced to the freezing point, and preferably the eutectic point, of such material if the latter were in or otherwise converted to a liquid state.

Thereafter, gamma radiation is applied to the protein material while at the reduced temperature and which temperature remains relatively constant during the period of irradiation. The gamma radiation is applied in an amount sufficient to destroy substantially all of the microbial contamination in the protein material. In addition, the amount of radiation which is generated in the radiation chamber is relatively constant during the entire radiation period, that is the rad amount of gamma radiation which is irradicated remains generally constant throughout the radiation period. Inasmuch as the temperature of the protein material has been reduced as indicated, the application of the gamma radiation does not siginificantly reduce the protein efficacy. In this way, it is possible to provide protein products which are relatively free of microbial contamination.

In a preferred aspect of the invention, the gamma radiation is applied in an amount of at least 5,000 rads and preferably in an amount of 600,000 rads. Generally, the gamma radiation will normally be applied in a range of about 600,000 rads to about 8,000,000 rads or higher. Preferably the radiation is applied in a range of about 600,000 rads to about 2,500,000 rads.

The microbial contamination which is to be destroyed is generally that of viral and bacterial contamination and mycoplasma contamination.

The protein material which is treated according to the invention is derived from or contained in animal or human body fluids which perform a biological function, and animal and human body cellular tissue which perform a biological function and protein material produced in or derived from an in-vitro environment using known biotechnology, such as in the production of insulin, and which exhibit biological activity. The invention is highly effective in, although not limited to elements of microbial contamination in those protein materials contained in or derived from extra cellular body liquids which may be, for example, cerebral spinal fluids, urine, synovial fluid, blood serum and amniotic fluid.

The term "microbial" with respect to contamination, as used herein is deemed to include all undesirable microorganisms and this is deemed to include all virus, whether or not virus are considered to be living organisms.

One of the principal aspects of the invention is that protein efficacy is not substantially adversely affected when treated with gamma radiation at the reduce temperature. The protein efficacy is measured or determined as opposed to protein activity since activity is not always measurable. For example, it may be difficult to measure the amount of oxygen carried by protein which is designed to carry oxygen. Further, the protein may be in a state where it cannot perform its normal function, but could perform its normal function if in a different state. Thus, efficacy is a measure or detection of what the protein is capable of doing compared to what it might do if in a normal state, and thus to some extent is a measure of activity.

This invention possesses many other advantages and has other purposes which may be made more clearly apparent from a consideration of the forms in which it may be embodied. These forms are described in detail in part of the present specification. They will now be described in detail for the purposes of more fully describing the general principals of the invention, but is it to be understood that such detailed descriptions are not to be taken in a limiting sense.

BRIEF DESCRIPTION OF THE DRAWING

In the accompanying drawing the FIGURE is a graphical illustration of migration activity of protein material as a function of density and charge for three different samples and as more fully described in Example V, hereinafter.

DETAILED DESCRIPTION OF PREFERRED EMBODIMENTS

In more detail, it has been found in accordance with the present invention, that it is possible to irradiate body serums and body tissues and other protein material at substantially reduced temperatures with gamma radiation without substantially adversely affecting the overall efficacy of the protein material. The various types of protein material which may be treated is hereinafter described in more detail.

As indicated above, the gamma radiation is applied in an amount of at least 5,000 rads and preferably in an amount of about 600,000 to about 8,000,000 rads or higher. In general there is no maximum amount of radiation which may be employed, except if it is so excessive to virtually destroy all protein efficacy. However, as a matter of practicality, most radiation should not exceed about 8,000,000, although it can. More preferably the radiation should not generally exceed about 2 million five hundred thousand rads so that the preferred range is about 600,000 rads to about 2 million five hundred thousand rads. If the gamma radiation were applied while the protein material was at, for example, ambient temperature, the material would be almost completely destroyed; that is the activity of the material would be rendered so low as to be virtually ineffective.

It has been found, unexpectedly, in accordance with the present invention, that if the temperature of the protein material, when in a non-lyophilized form, is reduced to the freezing temperature and preferably the eutectic temperature, the efficacy is not substantially adversely affected. With tissue or serum in a lyophilized form it is not necessary to reduce the temperature to the freezing or eutectic point, but the temperature should be reduced so that it is no higher than $-3$ degrees C., although reduction to the freezing or eutectic temperature is desirable. In other words, the lyophilized tissue or lyophilized serum should be reduced to at least the temperature equivalent to $-3$ degrees C. and preferably to the freezing point if the protein material were in a liquid form or reconstituted in a liquid form.

In accordance with the present invention, the protein materials are irradiated in an enclosed chamber and which is usually insulated to prevent harmful radiation from escaping from the chamber. When a core of radioactive material is pulled from a liquid bath, the amount of radiation which is generated remains relatively constant. While the amount of radiation may be reduced with the decaying half life of the core, that is during the period of time in which any sample is being irradiated, the radiation period is insignificantly small compared to the decaying half life of the core. Consequently, the radiation which is generated is effectively constant with respect to any vials of protein material. Furthermore, inasmuch as the protein material may be located in a particular position in the chamber and due to the overall confines of this chamber, the amount of radiation received by the protein sample is generally constant over the radiation period.

In some cases, it is desirable to move these samples of the protein material along a track way and where the distance from the source of the radiation could vary within the chamber. However, here again, due to the size of the chamber, the amount of radiation received is relatively constant. Furthermore, by continuous movement on this track way even if there were any substantial differences in the amount received at one position, compared to another position on the track way, the amount would be averaged and therefore generally constant after the complete irradiation period.

The temperature of the protein material when in the non-lyophilized state should always be below the freezing point, as aforesaid. However, it is more preferable to reduce the temperature of the non-lyophilized protein material to at least the eutectic temperature as opposed to the freezing temperature. It is recognized that activity of proteins are reduced proportionally with temperature reduction. however, there is a very substantial activity reduction when the protein material passes to a frozen state, and this is generally the state where the material becomes crystalline. It has also been recognized that there is a very substantial activity reduction when the temperature has been reduced to the eutectic point. Thus, it is desirable to reduce the temperature of the non-lyophilized material to at least the eutectic point.

It has also been found in connection with the present invention, that in most cases, both the freezing point and the eutectic point, or at least either the freezing point or eutectic point, will be below $-3$ degrees C. In some cases, it is desirable to reduce the temperature of the protein material to at least $-20$ degrees C. and in some cases to about $-70$ degrees C. This is particularly true when freezing the protein material before subjection to gamma radiation. However, no significant beneficial results have been found, to date, by reducing the temperature below $-70$ degrees C., although it is possible to reduce the temperature below $-70$ degrees C.

The term "non-lyophilized" with reference to the protein material generally includes all forms of protein material which may be treated in accordance with the present invention and which are not in a lyophilized form. Thus, "non-lyophilized" protein will include, at least, fluids such as serums, components, or sera, tissue and cells and proteins produced in an in-vitro environment. In essence, the lyophilized form of protein is merely a special case of the protein such that its powdered or dry state is believed to provide some resistance to gamma radiation and thus it is only necessary to reduce the temperature to $-3$ degrees C.

The present invention is effective in treating essentially all forms protein material which exhibit biological activity to destroy microbial contamination without substantially reducing protein efficacy. Preferably those protein materials include (1) protein materials derived from or contained in animal or human body fluids and which perform a biological function, (2) animal or human body cellular tissue which performs a biological function and (3) protein material grown in an in-vitro environment and which perform a biological function.

The fluids and tissues may be obtained from human beings or any of a number of animals normally used for this purpose, as for example, mice, sheep, kine, rabbits, etc. In many cases the protein material may be grown in or subjected to treatment in various body cavaties, such as the peritoneal cavity or in the blood system of animals and then extracted therefrom.

As indicated above, the invention is highly effective in destroying microbial contamination without substantially reducing protein efficacy in those protein derived from or contained in animal and fluid body fluids and particularly extra cellular body fluids. Some of the fluids which may be irradiated in accordance with the present invention are those body serums which include blood serum, cerebral spinal fluids, urine, saliva, synovial fluid, semen, amniotic fluid, perspiration and the like.

It is possible to irradiate with gamma radiation, either the whole serum or portions thereof. For example, with blood the whole plasma may be irradiated or certain of the elements, as for example, fibrinogen may be removed and the blood serum may be irradiated with other protein components therein. Otherwise, the various protein components in the blood serum may be extracated and irradiated apart from the serum. In many cases, and when irradiating certain plasmas or cells, e.g. red blood cells, it is desirable to add a suitable preservative to protect such plasmas or cells when reducing the temperature. This will prevent the breaking of the red blood cells and maintain the longevity.

The blood serum contains several protein materials which include for example, red blood cells, white cells, platelets, fibrinogen, albumin and gamma globulin and components that contain blood cloting factors, etc. As indicated, these components can be irradiated separately or while in the whole blood.

Many body tissues which are used for in-vitro application, e.g. testing any diagnostic applications, may be irradiated in accordance with the present invention to destroy any microbial contamination. For example, after certain tissue is removed from a body and before it is used in a testing or diagnostic application or in a transplant application it may be attacked by microbes, and thus for body tissue which may have been stored, it is desirable to remove such contamination.

It is also possible to irradiate various body tissue to potentially reduce possibility of rejection in transplants. It is believed that the process of the invention may be highly effective in reducing the immune responses of a body. For example, in many cases, bone marrow is used for transplanatation in leukemia patients. Thus it would be desirable to irradiate such bone marrow in order to not only reduce the possibility of microbial contamination, but also to reduce the possibility of rejection when transplanted. In a kidney transplant, if the organ is subjected to gamma radiation at a very reduced temperature, the immune response itself may be reduced. A great deal is not known about immunology and why the body responds with a rejection. However, it has been realized that this application of gamma radiation at reduced temperatures to the organ or tissue to be transplanted can reduce the immune response. Further, monoclonal antibodies can also be certified by irradiation in accordance with the present invention. Inasmuch as these antibodies are grown in the peritoneal cavity of animals, such as mice, or in tissue culture systems, and when mature the antibodies are used for injection into cancer patients, or for use in diagnostic reagents, it is highly desirable to certify such products as being viral free. The method of the present invention has been found to be highly effective in reducing the viral contamination in such monoclonal antibodies.

As indicated, it is also possible to effectively irradiate protein material produced in an in-vitro situation without substantially reducing efficacy of such protein material. For example, protein tissue cultures can be grown in an in-vitro situation and tissue culture sera are used in an in-vitro environment to suppport growth of the tissue culture. These tissues and sera are often used in diagnostic and testing applications and may be used to simulate in-vivo situations. However, they are also equally likely to be contaminated by microbes as any protein derived from or contained in a body tissue or fluid. The proces of the invention is also highly effective in destroying such microbial contamination in any protein thus grown in an in-vitro environment.

Temperature reduction of the protein material may be accomplished in several fashions. For example, the protein material can be merely refrigerated to the desired reduced temperature. In many cases, the material is inserted in sealed containers and stored in a ice bath. In many cases, it is desirable to reduce the temperature of a product slowly before reaching the freezing point. In other cases it is desired to reduce the temperature quickly, as for example by flash freezing. In all cases, the temperature of the material which is being irradiated will remain relatively constant during the radiation period. In cases of mechanical refrigeration, the temperature is established by a thermostat and remains at the preselected temperature. In the case of an ice bath or a bath of dry ice, the temperature, almost, by definition, remains the same since the radiation takes place in a period in which the ice bath is not completely melted and evaporated.

The protein activity will decrease somewhat after irradiation. However, it has been found that the activity decrease does not materially affect the usefulness of the contaminant free material. In generally all cases the activity is not reduced over 50% and this is acceptable for most purposes. Genrally the activity reduction does not exceed 60%. It is believed that usually the protein material can be rendered free of microbial contamination with only about a 25% activity reduction and in many cases only a 10% to 15% efficacy reduction. In some cases, no reduction in efficacy was found after irradiation in accordance with the present invention.

EXAMPLES

The invention is further illustrated by, but not limited to the following examples.

EXAMPLE I

The effects of gamma radiation on a factor VIII component of blood i.e., the antihemophyliac factor, was investigated in various states. Four vials of factor VIII serum was obtained from a known source in a lyophilized powder form. A portion of the lyophilized dry powder was introduced into a vial for Test Sample No. 1 and stored at room temperature.

Fifty mls of the factor VIII lyophilized component was reconstituted in 40 mils of water. The water was supplied by the same source. During reconstitution with this water supply a 1 of the lyophilized material went into solution. The reconstituted solution was then placed in a vial and designated to represent Test Sample No. 2.

The solution of the reconstituted factor VIII blood component was then frozen at −70 degrees C. in dry ice. A portion of the lyophilized factor VIII component was placed in a vial in its dry form and designated to represent Test Sample No. 3. Finally, another portion of the factor VIII component was placed in a vial and designated to represent Test Sample No. 4 which was a control sample and stored at room temperature.

The powder sample stored at room temperature, namely Test Sample No. 1 was irradiated at room temperature with 2.5 megarads of gamma radiation. The frozen liquid of Test Sample No. 2 was then irradiated with 2.5 megarads of gamma radiation. The powder containing the vial of Test Sample No. 3 which was supplied and not reconstituted, but stored at −70 degrees C. was also irradiated at −70 degrees C. with 2.5 megarads. The fourth sample, e.g. Test Sample No. 4, which was the control, was not irradiated.

The vials containing Test Samples No.'s 2 and 3 were packed in dry ice when irradiated and were still hard frozen at −70 degrees C. Both of the Test Samples No. 2 and 3 were continuously kept at −70 degrees C. before assay.

The control unit, namely Test Sample No. 4 was examined and demonstrated 350 units of activity. The liquid frozen unit of Test Sample No. 2 showed 170 units of activity, and the powder which was frozen in dry form, Test Sample No. 3 showed 180 units of activity. The powder irradiated at room temperature, Test Sample No. 1, disclosed only 30 units of activity.

The experiment showed that the reconstituted and dry samples which were frozen during irradiation revealed the best activity after irradiation, since biological activity in Test Sample No. 1 was virtually destroyed.

EXAMPLE II

The procedure of Example I is applied to packed red blood cells which is first suspended in glycerol. A first portion of the blood-glycerol suspension is placed in a vial as Test Sample No. 1 and stored at about 2 degrees C. to about 8 degrees C. A second portion of the blood-glycerol mixture is then reduced to freezing temperature slowly, at least to −3 degrees C. and placed in a vial as Test Sample No. 2 and is stored at −3 degrees C. Finally a control sample of the blood-glycerol mixture is stored at a temperature of 2 degrees C. to about 8 degrees C. Thereafter, each of the samples, except for the control sample are then irradiated. Efficacy of the frozen cells are similar to the control while there is esentially no efficacy to the sample irradiated at room temperature.

EXAMPLE III

The procedure of Example I is repeated, except that 800,000 rads of gamma radiation is applied to each of Test Samples No. 1-3. The activity in each case, is significantly greater. It is estimated that activities for the liquid frozen sample, namely Test Sample No. 2 and for the frozen powder sample, namely Test Sample No. 3 are each about 80%, i.e. 280. The activity for Test Sample No. 1, irradiated at room temperature, can be slightly higher, about 32-33. The activity of the control sample does not change.

EXAMPLE IV

The same procedure is employed as in Example I, except that 600,000 rads of gamma radiation is applied to each of Test Samples No. 1 through 3, but not the control sample, namely Test Sample No. 4. Again, all microbial contamination is essentially destroyed and the activities of each of the three irradiated samples are slightly higher than those in Example III. It is estimated that activities for the liquid frozen sample, namely Test Sample No. 2 and for the frozen powder sample, Test Sample No. 3, are each about 298. The activity for Test Sample No. 1 irradiated at room temperature remains about the same as that in Example III, namely 32-33 and the activity of the control sample, again, does not change.

EXAMPLE V

A sample of a calf serum offered under the trademark NEONATE by Biocell Laboratories, Inc. of Carson, Ca. was further tested for activity against a control. One vial of the calf serum sample was frozen and subjected to radiation in an amount of about 1.5 megarads. A second sample was irradiated at room temperature with the same radiation level. The third sample was a control which was not irradiated. The results of the change in charge of the protein are shown in the drawing which is a schematic view showing the distance of migration as a function of concentration on an electrophoretic gel for each of the three samples.

The protein material is placed on a gel in an electric field and measurements are made to determine the distance of movement as a function of the protein concentration. This provides a measure of movement activity of the protein and its electrical characteristics.

It can be seen from the drawing that the control sample and the frozen sample, after being irradiated, behaved very similarly, while the sample irradiated at room temperature behaved abnormally.

EXAMPLE VI

The calf serum of Example V was used as a nutrient to promote cell growth and replication. Approximately 10% of the serum was made with a conventional media, which was a solution containing various salts and amino acids.

One vial of the calf serum mixture was frozen and subjected to radiation in an amount of about 1.5 megarads. A second sample of the calf serum mixture was irradiated at room temperature with about 1.5 megarads. A third sample of the mixture was a control and was not irradiated. Each of the vials were known to contain a specific virus.

Upon examination, after irradiation the virus in the vial which was frozen and irradiated was completely destroyed. The virus in the sample irradiated at room temperature was also destroyed. The cell growth capability of the frozen mixture was not affected after irradiation. Cells were capable of growing or replicating in the frozen mixture after irradiation and when warmed to ambient temperature at the same rate as in the control sample which was not irradiated. However, cell growth or replication was almost non-existent in the sample which was irradiated at room temperature.

The process of the invention has been found to be highly effective in destroying essentially all forms of microbial contamination without substantially adversely affecting the protein activity. Thus, the invention provides a very effective and relatively inexpensive measure for certifying protein material as being free of microbial contamination, particularly when the material is intended for in-vivo use. Thus, the invention reduces the infectious rate with contagious diseases, particularly those contracted through blood transfusions, such as AIDS and hepatitis. In addition to the above, the invention is believed to be effective in reducing the immune response of a human or animal body when an organ or tissue to be transplanted has been treated according to the invention. The invention is also effective in destroying microbial contamination in tissue culture and tissue culture sera and other protein grown in an invitro situation.

Thus, there has been described a novel method for reducing microbial contamination in protein material by substantially reducing the temperature thereof and thereafter applying gamma radiation in an amount sufficient to destroy the microbial contamination and which does not substantially adversely affect the overall activity of the protein material. This method therefore fulfills all of the objects and advantages sought therefore. It should be understood that many changes, modifications, variations and other uses and applications will become apparent to those skilled in the art after considering this specification. Therefore, any and all such changes, modifications, variations and other uses and applications which become apparent to those skilled in the art after considering this specification are deemed to be covered by the invention which is limited only by the following claims.

Having thus described my invention, what I desire to secure and claims by letters patent is:

1. A method for destroying microbial contamination in protein material and rendering such material relatively free from such microbial contamination, said method comprising:
   (a) selecting protein material derived from or contained in (1) animal or human body fluids which perform a biological function, or (2) animal or human body cellular tissue which performs a biological function, or (3) protein material grown in or derived from an in-vitro environment and which performs a biological function,
   (b) reducing the temperature of such selected protein material to the freezing point of such protein material when in a non-lyophilized state, and reducing the temperature of such protein material when in a lyophilized state to a temperature of at least $-3$ degrees C.,
   (c) applying gamma radiation to said material at such reduced temperature and which temperature remains relatively constant during irradiation and where the gamma radiation is irradiated in a relatively constant rad amount during irradiation but which is sufficient to destroy substantially all microbial contamination in such protein material without substantially reducing protein efficacy, to thereby provide a protein material relatively free of microbial contamination and which still exhibits substantial biological efficacy.

2. The method for destroying microbial contamination of claim 1 further characterized in that said microbial contamination comprises virus contamination, bacterial contamination and mycoplasma contamination.

3. The method for destroying microbial contamination of claim 1 further characterized in that the temperature of the non-lyophilized protein material is reduced to at least the eutectic point of the protein material.

4. The method for destroying microbial contamination of claim 1 further characterized in that the temperature of the protein product is reduced to about $-70$ degrees C.

5. The method for destroying microbial contamination of claim 1 further characterized in that the minimum amount of gamma radiation is 5,000 rads.

6. The method for destroying microbial contamination of claim 1 further characterized in that the minimum amount of gamma radiation is 600,000 rads.

7. The method for destroying microbial contamination of claim 1 further characterized in that the gamma radiation is applied in a range of about 600,000 rads to about 2,500,000 rads.

8. The method for destroying microbial contamination of claim 1 further characterized in that the body fluids are extra-cellular body liquids.

9. The method for destroying microbial contamination of claim 1 further characterized in that the protein material is contained in or derived from an extra-cellular body liquid selected from the class consisting of cerebral spinal fluid, urine, synorial fluid, blood serum, and amniotic fluid.

10. A method for destroying microbial contamination in protein material and rendering such material relatively free from such microbial contamination, said method comprising:
    (a) selecting protein material derived from or contained in extra-cellular animal or human body fluids and which performs a biological function,
    (b) reducing the temperature of such body fluids at least to the freezing point of such fluids, and
    (c) applying gamma radiation to said material at such reduced temperature and which temperature remains relatively constant during irradiation and where the gamma radiation is irradicated in a relatively constant rad amount during irradiation of at about 5,000 rads to destroy substantially all microbial contamination in such protein material without substantially reducing protein efficacy, to thereby provide a protein material relatively free of microbial contamination and which still exhibits substantial biological efficacy.

11. The method of claim 10 further characterized in that said microbial contamination comprises virus contamination, bacterial contamination and mycoplasma contamination.

12. The method of claim 10 further characterized in that the temperature of the fluids is reduced to the eutectic point of the material.

13. The method of claim 10 further characterized in that the minimum amount of gamma radiation is 600,000 rads.

14. The method of claim 10 further characterized in that the gamma radiation is applied in a range of about 600,000 rads to about 2,500,000 rads.

15. The method of claim 10 further characterized in that the protein material is contained in or derived from an extracellular body liquid selected from the claim consisting of cerebral spinal fluid, urine, synorial fluid, blood serum, and amniotic fluid.

16. A method for destroying microbial contamination in protein material and rendering such material relatively free from such microbial contamination, said method comprising:
    (a) selecting protein material derived from or contained in (1) animal or human body fluids which perform a biological function, or (2) animal or human body cellular tissue which performs a biological function, or (3) protein material grown in or derived from an in-vitro environment and which performs a biological function,
    (b) reducing the temperature of such selected protein material to the eutetic point temperature of such protein material when in a non-lyophilized state, and reducing the temperature of such protein material when in a lyophilized state to a temperature equivalent to a eutectic point temperature if such material were in a non-lypholized state,
    (c) applying gamma radiation to said material at such reduced temperature and which temperature remains relatively constant during irradiation and where the gamma radiation is irradiated in a relataively constant rad amount during irradiation which is sufficient to destroy substantially all microbial contamination in such protein material without substantially reducing protein efficacy, to thereby provide a protein material relatively free of microbial contamination and which still exhibits substantial biological efficacy.

17. The method for destroying microbial contamination of claim 16 further characterized in that the minimum amount of gamma radiation is 5,000 rads.

18. The method for destroying microbial contamination of claim 16 further characterized in that the minimum amount of gamma radiation is 600,000 rads.

19. The method for destroying microbial contamination of claim 16 further characterized in that the gamma radiation is applied in a range of about 600,000 rads to about 2,500,000 rads.

* * * * *